United States Patent [19]
Davis et al.

[11] Patent Number: 5,266,490
[45] Date of Patent: Nov. 30, 1993

[54] MAMMALIAN EXPRESSION VECTOR

[75] Inventors: Samuel Davis, New York; George D. Yancopoulos, Briarcliff Manor, both of N.Y.

[73] Assignee: Regeneron Pharmaceuticals, Inc., Tarrytown, N.Y.

[21] Appl. No.: 678,408

[22] Filed: Mar. 28, 1991

[51] Int. Cl.$^5$ .................. C12N 15/79; C12N 15/12; C12N 15/18
[52] U.S. Cl. .................. 435/320.1; 536/23.4; 536/23.5; 536/24.1
[58] Field of Search .......... 435/320.1, 69.1, 172.3; 536/27, 24.1, 23.4, 23.5

[56] References Cited
PUBLICATIONS

Alt et al. (1978), J. Biol. Chem. 253(5):1357–1370.
Andersson et al. (1989), J. Biol. Chem. 264(14): 8222–8229.
Aruffo et al. (1989), J. Immunol. 143(5): 1723–1730.
Aruffo et al. (1987), Proc. Nat. Acad. Sci USA 84: 8573–8577.
Bebbington et al. (1987), DNA Cloning: A Practical Approach, vol. 3, Chapter 8, pp. 163–168, 188.
Boulay et al. (1990), Biochem. Biophys. Res. Comm. 168(3): 1103–1109.
Cunningham et al. (1991), Science 254: 821–825.
Kenny et al. (1989), SV40 DNA Replication In Vitro, NATO AS1 Series, vol. 434, pp. 437–448.
Maniatis et al. (1990), Molecular Cloning: A Laboratory Manual, vol. 2, pp. 16.3–16.81.
Martson (1987), DNA Cloning: A Practical Approach, vol. 3, Chap. 4, pp. 59–88.
Mizushima et al. (1990), Nucl. Acids Res. 18 (17): 5322.
Sambrook et al. (1988), Focus 10(3): 41–48.
Simmons et al. (1988), J. Immunol. 141 (8): 2797–2800.
Spector (1985), Genet. Engineering 7: 199–234.
Stamenkovic et al. (1988), J. Exp. Med. 167: 1975–1980.
Urlaub et al. (1980), Proc. Nat. Acad. Sci USA 77(7): 4216–4220.
Woeltje et al. (1990), J. Biol. Chem. 265 (18): 10720–10725.
Wysocki et al. (1978); Proc. Nat. Acad. Sci USA 75(6): 2844–2848.
Seed, B. (Oct. 1987), Nature, vol. 329, pp. 840–842.
Yanisch–Perron et al. (1985), Gene, vol. 33, pp. 103–119.
Seed et al. (May, 1987), Proc. Nat. Acad. Sci USA, vol. 84, pp. 3365–3369.

*Primary Examiner*—Richard A. Schwartz
*Assistant Examiner*—Philip W. Carter
*Attorney, Agent, or Firm*—Pennie & Edmonds

[57] ABSTRACT

DNA plasmid expression vector, pCMX, enables cDNA expression cloning in mammalian cell culture. This novel expression vector exhibits a marked increase in gene expression when compared to its parental plasmid construction.

7 Claims, 7 Drawing Sheets

```
ACGCGTTGAC ATTGATTATT GACTAGTTAT TAATAGTAAT CAATTACGGG GTCATTAGTT    60

CATAGCCCAT ATATGGAGTT CCGCGTTACA TAACTTACGG TAAATGGCCC CGCCTGGCTG   120

ACCGCCCAAC GACCCCCGCC CATTGACGTC AATAATGACG TATGTTCCCA TAGTAACGCC   180

AATAGGGACT TTCCATTGAC GTCAATGGGT GGACTATTTA CGGTAAACTG CCCACTTGGC   240

AGTACATCAA GTGTATCATA TGCCAAGTAC GCCCCCTATT GACGTCAATG ACGGTAAATG   300

GCCCGCCTGG CATTATGCCC AGTACATGAC CTTATGGGAC TTTCCTACTT GGCAGTACAT   360

CTACGTATTA GTCATCGCTA TTACCATGGT GATGCGGTTT TGGCAGTACA TCAATGGGCG   420

TGGATAGCGG TTTGACTCAC GGGGATTTCC AAGTCTCCAC CCCATTGACG TCAATGGGAG   480

TTTGTTTTGG CACCAAAATC AACGGGACTT TCCAAAATGT CGTAACAACT CCGCCCCATT   540

GACGCAAATG GGCGGTAGGC GTGTACGGTG GGAGGTCTAT ATAAGCAGAG CTCTCTGGCT   600

AACTAGAGAA CCCACTGCTT ACTGGCTTAT CGAAATTAAT ACGACTCACT ATAGGGAGAC   660

CGGAAGCTTC TAGAGATCCC TCGACCTCGA GATCCATTGT GCTGGCGCGG ATTCTTTATC   720

ACTGATAAGT TGGTGGACAT ATTATGTTTA TCAGTGATAA AGTGTCAAGC ATGACAAAGT   780

TGCAGCCGAA TACAGTGATC CGTGCCGCCC TAGACCTGTT GAACGAGGTC GGCGTAGACG   840

GTCTGACGAC ACGCAAACTG GCGGAACGGT TGGGGGTTCA GCAGCCGGCG CTTTACTGGC   900

ACTTCAGGAA CAAGCGGGCG CTGCTCGACG CACTGGCCGA AGCCATGCTG GCGGAGAATC   960

ATAGCACTTC GGTGCCGAGA GCCGACGACG ACTGGCGCTC ATTTCTGACT GGGAATGCCC  1020

GCAGCTTCAG GCAGGCGCTG CTCGCCTACC GCCAGCACAA TGGATCTCGA GGGATCTTCC  1080
```

FIG.1A

```
ATACCTACCA GTTCTGCGCC TGCAGGTCGC GGCCGCGACT CTAGAGGATC TTTGTGAAGG  1140

AACCTTACTT CTGTGGTGTG ACATAATTGG ACAAACTACC TACAGAGATT TAAAGCTCTA  1200

AGGTAAATAT AAAATTTTTA AGTGTATAAT GTGTTAAACT ACTGATTCTA ATTGTTTGTG  1260

TATTTTAGAT TCCAACCTAT GGAACTGATG AATGGGAGCA GTGGTGGAAT GCCTTTAATG  1320

AGGAAAACCT GTTTTGCTCA GAAGAAATGC CATCTAGTGA TGATGAGGCT ACTGCTGACT  1380

CTCAACATTC TACTCCTCCA AAAAGAAGA GAAAGGTAGA AGACCCCAAG GACTTTCCTT  1440

CAGAATTGCT AAGTTTTTTG AGTCATGCTG TGTTTAGTAA TAGAACTCTT GCTTGCTTTG  1500

CTATTTACAC CACAAAGGAA AAAGCTGCAC TGCTATACAA GAAAATTATG GAAAAATATT  1560

CTGTAACCTT TATAAGTAGG CATAACAGTT ATAATCATAA CATACTGTTT TTTCTTACTC  1620

CACACAGGCA TAGAGTGTCT GCTATTAATA ACTATGCTCA AAAATTGTGT ACCTTTAGCT  1680

TTTTAATTTG TAAAGGGGTT AATAAGGAAT ATTTGATGTA TAGTGCCTTG ACTAGAGATC  1740

ATAATCAGCC ATACCACATT TGTAGAGGTT TTACTTGCTT TAAAAAACCT CCCACACCTC  1800

CCCCTGAACC TGAAACATAA AATGAATGCA ATTGTTGTTG TTAACTTGTT TATTGCAGCT  1860

TATAATGGTT ACAAATAAAG CAATAGCATC ACAAATTTCA CAAATAAAGC ATTTTTTTCA  1920

CTGCATTCTA GTTGTGGTTT GTCCAAACTC ATCAATGTAT CTTATCATGT CTGGATCCTT  1980

ACTCCGCCCA TCCCGCCCCT AACTCCGCCC AGTTCCGCCC ATTCTCCGCC CCATGGCTGA  2040
```

FIG. 1B

```
CTAATTTTTT TTATTTATGC AGAGGCCGAG GCCGCCTCGG CCTCTGAGCT ATTCCAGAAG 2100

TAGTGAGGAG GCTTTTTTGG AGGCCTAGGC TTTTGCAAAA AGGAGCTCCC AGCAAAAGGC 2160

CAGGAACCGT AAAAAGGCCG CGTTGCTGGC GTTTTTCCAT AGGCTCCGCC CCCCTGACGA 2220

GCATCACAAA AATCGACGCT CAAGTCAGAG GTGGCGAAAC CCGACAGGAC TATAAAGATA 2280

CCAGGCGTTT CCCCCTGGAA GCTCCCTCGT GCGCTCTCCT GTTCCGACCC TGCCGCTTAC 2340

CGGATACCTG TCCGCCTTTC TCCCTTCGGG AAGCGTGGCG CTTTCTCAAT GCTCACGCTG 2400

TAGGTATCTC AGTTCGGTGT AGGTCGTTCG CTCCAAGCTG GGCTGTGTGC ACGAACCCCC 2460

CGTTCAGCCC GACCGCTGCG CCTTATCCGG TAACTATCGT CTTGAGTCCA ACCCGGTAAG 2520

ACACGACTTA TCGCCACTGG CAGCAGCCAC TGGTAACAGG ATTAGCAGAG CGAGGTATGT 2580

AGGCGGTGCT ACAGAGTTCT TGAAGTGGTG GCCTAACTAC GGCTACACTA GAAGGACAGT 2640

ATTTGGTATC TGCGCTCTGC TGAAGCCAGT TACCTTCGGA AAAAGAGTTG GTAGCTCTTG 2700

ATCCGGCAAA CAAACCACCG CTGGTAGCGG TGGTTTTTTT GTTTGCAAGC AGCAGATTAC 2760

GCGCAGAAAA AAAGGATCTC AAGAAGATCC TTTGATCTTT TCTACGGGGT CTGACGCTCA 2820

GTGGAACGAA AACTCACGTT AAGGGATTTT GGTCATGAGA TTATCAAAAA GGATCTTCAC 2880

CTAGATCCTT TTAAATTAAA AATGAAGTTT TAAATCAATC TAAAGTATAT ATGAGTAAAC 2940

TTGGTCTGAC AGTTACCAAT GCTTAATCAG TGAGGCACCT ATCTCAGCGA TCTGTCTATT 3000
```

FIG.1C

```
TCGTTCATCC ATAGTTGCCT GACTCCCCGT CGTGTAGATA ACTACGATAC GGGAGGGCTT    3060

ACCATCTGGC CCCAGTGCTG CAATGATACC GCGAGACCCA CGCTCACCGG CTCCAGATTT    3120

ATCAGCAATA AACCAGCCAG CCGGAAGGGC CGAGCGCAGA AGTGGTCCTG CAACTTTATC    3180

CGCCTCCATC CAGTCTATTA ATTGTTGCCG GGAAGCTAGA GTAAGTAGTT CGCCAGTTAA    3240

TAGTTTGCGC AACGTTGTTG CCATTGCTAC AGGCATCGTG GTGTCACGCT CGTCGTTTGG    3300

TATGGCTTCA TTCAGCTCCG GTTCCCAACG ATCAAGGCGA GTTACATGAT CCCCCATGTT    3360

GTGCAAAAAA GCGGTTAGCT CCTTCGGTCC TCCGATCGTT GTCAGAAGTA AGTTGGCCGC    3420

AGTGTTATCA CTCATGGTTA TGGCAGCACT GCATAATTCT CTTACTGTCA TGCCATCCGT    3480

AAGATGCTTT TCTGTGACTG GTGAGTACTC AACCAAGTCA TTCTGAGAAT AGTGTATGCG    3540

GCGACCGAGT TGCTCTTGCC CGGCGTCAAT ACGGGATAAT ACCGCGCCAC ATAGCAGAAC    3600

TTTAAAAGTG CTCATCATTG GAAAACGTTC TTCGGGGCGA AAACTCTCAA GGATCTTACC    3660

GCTGTTGAGA TCCAGTTCGA TGTAACCCAC TCGTGCACCC AACTGATCTT CAGCATCTTT    3720

TACTTTCACC AGCGTTTCTG GGTGAGCAAA AACAGGAAGG CAAAATGCCG CAAAAAAGGG    3780

AATAAGGGCG ACACGGAAAT GTTGAATACT CATACTCTTC CTTTTTCAAT ATTATTGAAG    3840

CATTTATCAG GGTTATTGTC TCATGAGCGG ATACATATTT GAATGTATTT AGAAAAATAA    3900

ACAAATAGGG GTTCCGCGCA CATTTCCCCG AAAAGTGCCA CCTG                     3944
```

MAMMALIAN EXPRESSION VECTOR

1. INTRODUCTION

The present invention relates to the construction and utilization of a DNA plasmid vector, in particular, pCMX. This vector promotes the expression of cloned genes when transfected into mammalian cell lines. The functional portions of pCMX include the immediate early promoter of human cytomegalovirus (HCMV), a "polylinker" sequence facilitating the insertional cloning of DNA sequences, an RNA splice and polyadenylation signal, origins of replication from SV40 (for replication in COS cells) and pBR322 (for replication in E. coli), and the gene encoding β-lactamase, a selectable marker conferring resistance to ampicillin in bacterial cells. The invention can be used to transiently or stably express eukaryotic genes within mammalian cells, that can provide an environment conducive to appropriate protein folding or other eukaryotic protein modifications such as glycosylation and oligomerization.

2. BACKGROUND OF THE INVENTION

The advent of recombinant DNA technology in the 1970's led to the isolation of a myriad of DNA sequences that encode useful proteins. The in vitro expression of cloned eukaryotic genes in mammalian cells is well documented. (for review, see (1) Maniatis, et al., 1990, In: *Molecular Cloning: A Laboratory Manual*; Vol. II, Chapter 16; (2) Bebbington and Hentschel, 1987, In: *DNA Cloning* Vol III: A Practical Approach, Ed., Glover, O. M., pp. 163-188; (3) Sambrook and Gething, 1988, Focus 10(3):41-48). The utilization of eukaryotic expression systems has led to an increased understanding of eukaryotic promoter strength, intron function, RNA splicing and polyadenylation functions as well as transport phenomena of newly synthesized polypeptides. However, a more practical application of in vitro eukaryotic expression systems is the cloning of novel cDNAs as well as the overproduction and isolation of novel gene products. Expression of eukaryotic proteins in eukaryotic hosts more readily allows production of functional proteins correctly folded and modified (e.g., via glycosylation and acetylation, for example).

Two basic types of mammalian expression systems have been developed to date. The first involves viral expression vectors modified to express a gene of interest (for a review, see Muzyczka, 1989, Current Topics in Microbiology and Immunology). This modification usually encompasses the replacement of a portion of the viral genome with the gene of interest. The functions lost in cis from the viral genome are complemented by cloning this deleted genomic region into a separate "helper plasmid". Therefore, co-transfection of both recombinant vectors results in propagation of the virus as well as overproduction of the protein of interest. The second type of mammalian gene expression system involves the construction of DNA plasmid vectors possessing the capacity to express cloned inserts in mammalian cells. The expression of the cloned gene may occur in a transient, extrachromosomal manner or through the stable transformation of the respective mammalian host cell line. The typical mammalian expression vector will contain (1) regulatory elements, usually in the form of viral promoter or enhancer sequences and characterized by a broad host and tissue range; (2) a "polylinker" sequence, facilitating the insertion of a DNA fragment within the plasmid vector; and (3) the sequences responsible for intron splicing and polyadenylation of mRNA transcripts. This contiguous region of the promoter-polylinker-polyadenylation site is commonly referred to as the transcription unit. The vector will also contain (4) a selectable marker gene(s) (e.g., the β-lactamase gene), often conferring resistance to an antibiotic (such as ampicillin), allowing selection of initial positive transformants in E. Coli; and (5) sequences facilitating the replication of the vector in both bacterial and mammalian hosts.

An example of such an expression vector is CDM8 (Seed, 1987, Nature 329: 840-842; Seed and Aruffo, 1987, Proc. Natl. Acad. Sci. USA 84: 3365-3369; Aruffo and Seed, Proc. Natl. Acad. Sci. USA 84: 8573-8577), the parental plasmid to the pCMX plasmid of the present invention. The transcription unit of CDM8 is composed of a chimeric promoter (the human cytomegalovirus AD169 constitutive promoter fused to the T7 RNA polymerase promoter), a polylinker region and the SV40 small tumor (t) antigen splice and early region polyadenylation signals derived from pSV2. The human cytomegalovirus (HCMV) promoter is expressed in a variety of mammalian cell types, while the T7 bacteriophage DNA-dependent RNA polymerase promoter can drive in vitro cell-free transcription/translation of cloned inserts. This particular promoter fusion allows initial experiments to be conducted within the confines of the host mammalian cell type, while further analysis and utilization of the cloned insert may potentially be carried out in an in vitro "cell-free" transcription/translation system. The constitutively expressed HCMV promoter has also been utilized in other mammalian expression vectors besides CDM8 (for example, see Andersson, et al., 1989, J. Biol. Chem. 264(14):8222-8229). Origins of replication in CDM8 include (1) πVX (allowing e.g., replication in E. coli) (2) SV40 origin (allowing e.g., replication in a variety of COS cell types) (3) polyoma origin (allowing e.g., replication in polyoma virus transformed mouse fibroblasts) and (4) the bacteriophage M13 origin (allowing e.g., generation of single-stranded template for DNA sequence analysis and/or oligonucleotide site-directed mutagenesis). Finally, CDM8 carries the supF gene for selection in E. coli. In this antibiotic selection system, a CDM8-based plasmid construction is transformed into a specialized E. coli strain containing an episome carrying genes encoding resistance to the antibiotics, ampicillin and tetracyline. However, both genes contain chain termination ("nonsense" codon) point mutations inactivating the resistance phenotype. The supF gene product, a nonsense suppressor tRNA, restores the resistant phenotype for each antibiotic. Therefore, selection is based on growth of the specialized episomal-carrying E. coli strain on media containing ampicillin and tetracycline. Colonies exhibiting this phenotype are supposedly transformed with the CDM8-based plasmid construction.

The CDM8 vector is compatible with COS cell lines as well as cell lines transformed with the polyoma virus. COS cell lines are African green monkey CV1 cells transformed with an origin-defective SV40 mutant virus. The COS cells produce the large T antigen, which is required in trans to promote replication of SV40 or plasmid constructions such as CDM8 which contain the respective cis-acting sequences initiating viral replication. Therefore, COS cells transfected with a CDM8-based construction will support replication of the plasmid, resulting in increased plasmid copy number and a transient overexpression of the gene of interest.

The major use of CDM8 is cDNA expression cloning and overproduction of specific proteins in a mammalian in vitro expression system. Expression cloning takes on various forms depending on the mode of detection utilized to identify the cDNA of interest (see discussion, infra). However, the initial step consists of isolating mRNA and synthesizing double-stranded deoxyribonucleic acid copies of the mRNA population (cDNAs). These cDNAs must be efficiently ligated to a plasmid or bacteriophage DNA cloning vector and transferred to the appropriate host prior to library screening and analysis. CDM8 contains two BstXI restriction sites, making it amenable to the "adaptor" linker procedure of ligating cDNAs to the vector, i.e., the use of DNA fragments blunt ended at one end (and therefore compatible for ligation with the blunt ended cDNA) but containing a non-palindromic overhang on the other end (in this instance, compatible for ligation with BstXI digested vector DNA, but not with other cDNAs).

A cDNA mammalian expression library may be utilized in several ways to pursue the identification and isolation of novel cDNAs (see Chapter 16 of Maniatis, et al., supra for a review). Briefly, cDNA libraries are transfected into the appropriate cell lines. A secreted gene product may be identified by a variety of assay techniques. Seed (1987, Nature 329:840–842) utilized the CDM8-based cDNA expression system (Seed and Aruffo, 1987, Proc. Natl. Acad. Sci. USA 84:3365–3369) to select cDNAs encoding novel surface membrane proteins. These cDNA expression proteins integrated on the cell surface and were selected by the ability of that cell type to bind to specific antibody coated dishes. Positive cell types were collected, the plasmids rescued and subsequently transformed into *E. coli* for further analysis.

The main drawback of CDM8 involves several problems present when utilizing the supF based antibiotic system for selecting transformed *E. coli* cells. First, the host *E. coli* strain displays a relatively high frequency of antibiotic resistance, so that there is often an unacceptably high background of bacterial colonies lacking plasmid sequences. Second, low yields of bacterial plasmid DNA derived from these host-specific strains are problematic if reversion occurs during the growth of a bacterial culture. Third, plasmid preparations frequently become contaminated with episomal DNA that contains the genes conferring resistance to ampicillin and tetracycline. Fourth, the requirement of specific genes conferring antibiotic resistance encompassed within an episome drastically reduces the *E. coli* host range.

A second common bacterial vector also utilized as a parental plasmid to the pCMX plasmid of the present invention is pGEM4Z (Promega Bulletin 036, 1988), which contains a pUC derived β-lactamase gene and pBR322 origin of replication. pBR or pUC based plasmid constructions (Yanisch-Perron, et al., 1985, Gene 33:103–109) are widely used bacterial vectors.

3. SUMMARY OF THE INVENTION

The invention relates to the construction of a DNA plasmid mammalian expression vector, in particular, pCMX. The DNA plasmid expression vector of the present invention retains the principal advantages of plasmid CDM8 without its inherent disadvantages. The vector of the present invention is far more efficient than CDM8 with regard to the quality and quantity of transiently and stably expressed proteins, and its use for cDNA expression cloning as well as overexpression of genes of interest.

The functional components of the plasmid of the invention are (1) the immediate early promoter of HCMV, (2) an SV40 RNA splice/polyadenylation sequence, (3) an SV40 origin of replication, (5) a pBR322 origin of replication and (4) a selectable marker conferring resistance to an antibiotic. In particular, the β-lactamase gene conferring resistance to the antibiotic ampicillin can be used.

The invention can be utilized for, but is not limited to, the transient expression of a cloned DNA sequence in transfected COS cells. While the examples presented utilize a COS cell line, the invention is not limited to one particular mammalian cell line. Any mammalian cell type expressing the large T antigen of SV40 (see discussion of COS cell types, supra) may potentially support replication and, hence, expression of pCMX-based constructions. Additionally, pCMX derived constructions may be used to produce mammalian cell lines that stably express a recombinant protein. For example, pCMX-derived constructions can be co-transfected with another plasmid(s) containing an appropriate dominant selectable marker(s) to isolate cell lines overproducing the cloned gene product.

The invention can be utilized to isolate novel cDNAs via expression in transfected mammalian cells, i.e., by cDNA expression cloning. This technique is exemplified in the isolation and characterization of a cDNA encoding the ciliary neurotrophic factor receptor (CNTFR) using pCMX as a mammalian expression vector. cDNA expression cloning is a technique whereby a population of purified mRNA is transcribed into double stranded complementary DNA sequences (cDNA); ligated into a DNA plasmid expression vector (under the control of a constitutive or inducible promoter); transferred into the appropriate prokaryotic or eukaryotic host to form a representative "library" of cDNA clones; screened on the basis of a characteristic of the protein product encoded by the desired cDNA expressed by individual cells within the population; thus resulting in positive clones being purified, characterized and amplified (see Section 2, supra, for additional discussion). One embodiment of this technique involves expression of cDNA clones in a mammalian cell population and selection of novel cDNAs on the ability of the cell type expressing that particular cDNA to interact with an antibody or ligand, capable of specific binding to the encoded product of that cDNA, which has been previously bound to a solid support such as a petri dish. Positive cDNAs (those expressed in cell types binding to the solid support) are recovered, transformed into a convenient host (e.g., *E. coli*) and characterized by known recombinant DNA techniques. This procedure, referred to as "panning" (Wysocki and Sata, 1979, Proc. Natl. Acad. Sci. USA 75:2844–2848; Seed and Aruffo, 1987, Proc. Natl. Acad. Sci. USA 84:3365–3369) may become a more powerful technique due to increased expression of the cloned cDNA insert as provided by the improved vector of the present invention, pCMX. In other words, a cell line possessing a low affinity to the antibody or ligand (through expression of the cDNA) might yield a stronger signal due to increased cDNA expression, thus culminating in the cloning of novel cDNAs unobtainable via the use of previously available cDNA expression plasmids.

In another embodiment, the invention is utilized to overproduce a proteinaceous product of a cloned DNA fragment inserted in a polylinker sequence located between the HCMV promoter and the 3' splice/polyadenylation signal. In a specific embodiment, the invention describes the increased expression of an antigenically tagged derivative of nerve growth factor, designated NGF-myc, in pCMX in relation to NGF-myc produced in a parental plasmid construction.

3.1 DEFINITIONS

The terms listed below, as used herein, will have the meanings indicated.

NGF—myc—nerve growth factor—myc fusion construction
PCR—polymerase chain reaction
tRNA—transfer ribonucleic acid
DMEM—Dulbecco's modified Eagles medium
CNTFR—ciliary neurotrophic factor receptor
MTX—methotrexate
DRG—dorsal root ganglion
ITS—insulin—transferrin—selinite

4. DESCRIPTION OF THE FIGURES

FIGS. 1(A-D): Nucleotide sequence of pCMX (SEQ ID NO: 1)

5. DETAILED DESCRIPTION OF THE INVENTION

The invention relates to the construction of a novel DNA plasmid expression vector, in particular, pCMX. The functional components of the plasmid of the invention are (1) sequences including the immediate early promoter of HCMV, (2) an SV40 RNA splice/polyadenylation sequence, (3) an SV40 origin of replication, (5) a pBR322 origin of replication and (4) a selectable marker conferring resistance to an antibiotic. In particular, the β-lactamase gene conferring resistance to the antibiotic ampicillin can be used. In a specific embodiment, the immediate early promoter of HCMV (a promoter active in mammalian cells) is fused to the T7 phage RNA polymerase promoter; this embodiment thus allows, e.g., for in vitro cell free expression under control of the T7 promoter.

The invention can be utilized to isolate novel cDNAs via expression in transfected mammalian cells, i.e., by cDNA expression cloning. This technique is exemplified in the isolation and characterization of a cDNA encoding the ciliary neurotrophic factor receptor (CNTFR) using pCMX as a mammalian expression vector. cDNA expression cloning is a technique whereby a population of purified mRNA is transcribed into double stranded complementary DNA sequences (cDNA); ligated into a DNA plasmid expression vector (under the control of a constitutive or inducible promoter); transferred into the appropriate prokaryotic or eukaryotic host to form a representative "library" of cDNA clones; screened and selected on the basis of immunological, enzymatic, phenotypic, functional, or other characteristics of the protein product encoded by the desired cDNA; resulting in positive clones being purified, characterized and amplified (see Section 2, supra, for additional discussion). One embodiment of this technique involves expression of cDNA clones in a mammalian cell population and selection of novel cDNAs on the ability of the cell type expressing that particular cDNA to interact with an antibody or ligand, capable of specific binding to the encoded product of that cDNA, which has been previously bound to a solid support such as a petri dish. Positive cDNAs (those expressed in cell types binding to the solid support) are recovered, transformed into a more amenable host (e.g., E. coli) and characterized by known recombinant DNA techniques. This procedure, referred to as "panning" (Wysocki and Sata, 1979, Proc. Natl. Acad. Sci. USA 75:2844-2848; Seed and Aruffo, 1987, Proc. Natl. Acad. Sci. USA 84:3365-3369) may become a more powerful technique due to increased expression of the cloned cDNA insert as provided by the improved vector, pCMX. In other words, a cell line possessing a low affinity to the antibody or ligand (through expression of the cDNA) might yield a stronger signal due to increased cDNA expression, thus culminating in the cloning of novel cDNAs unobtainable via the use of previously available cDNA expression plasmids.

Specific embodiments of the invention include, but are not limited to, the use of pCMX in expression cloning in which the cDNA is selected based not on antigenic properties of the expressed protein, but on other characteristics such as biological activity. For example, if the expressed product is secreted, the selection can be based on the biological activity of the pooled cell supernatants. Altered cell phenotype in transformed cell lines, (see discussion, supra), etc. can also be the basis for selection.

In another embodiment, the invention can be utilized to overproduce a proteinaceous product of a cloned DNA fragment inserted in a polylinker sequence located between the HCMV promoter and the 3' splice/polyadenylation signal. In a specific embodiment, the invention describes the increased expression of NGF-myc in pCMX in relation to NGF-myc produced in a parental plasmid construction.

The invention can be utilized for, but is not limited to, the transient expression of a cloned DNA sequence in transfected COS cells. While the examples presented utilize a COS cell line, the invention is not limited to one particular mammalian cell line. Any mammalian cell type expressing the large T antigen of SV40 (see discussion of COS cell types, supra) may potentially support replication and, hence, expression of pCMX-based constructions.

Additionally, stable mammalian cell lines may be chosen in which pCMX derived constructions are co-transfected with another plasmid(s) containing an appropriate dominant selectable marker(s) utilized to isolate cell lines overproducing the cloned gene product. By way of example but not limitation, CHO cells deficient in both alleles of the dihydrofolate reductase (dhfr) gene (Urlaub and Chasin, 1980, Proc. Natl. Acad. Sci. USA 77:4216-4220) may be co-transfected with a pCMX-based construction and a plasmid carrying the dhfr gene under control of a weak promoter. The resulting co-transformants will result in individual colonies resistant to the selective pressure of nucleoside-free media. Such colonies are then treated with methotrexate (MTX) to induce gene amplification (Alt, et al., 1978, J. Biol. Chem. 253: 357–1370). MTX-resistant individual colonies may then be isolated and screened for an amplified CHO transformant overexpressing the cloned insert of interest. In another embodiment, 3T3 cells may be transfected for stable expression.

In the present invention, the plasmid pCMX supports expression of a cloned DNA sequence. The invention is illustrated by way of working examples in which the expression of NGF-myc in both pCMX and CDM8 demonstrates the increased utility of pCMX to express eukaryotic genes in mammalian cells. The invention is not limited to the expression of NGF-myc, but to any genomic, cDNA or other DNA sequence inserted 3' to the aforementioned promoter element in such a fashion as to result in the synthesis of a stable RNA transcript. In a further embodiment of the invention, the presence of a functional T7 phage RNA polymerase promoter permits use of the pCMX vector outside the confines of a host mammalian cell. This promoter drives in vitro cell-free transcription/translation of DNA inserts cloned downstream from the HCMV/T7 promoter fusion.

The transcription unit of pCMX is unchanged from CDM8. The HCMV promoter constitutively expresses downstream DNA sequences. A polylinker region containing multiple cloning sites facilitates insertion cloning of the DNA sequence of interest proximal to the HCMV promoter. Further downstream is an SV40 splice/polyadenylation signal. Additionally, both pCMX and CDM8 contain an SV40 origin of replication and pBR322 (the $\pi$VX origin of replication in pCDM8 is identical to the pBR322 origin of replication) origin of replication. The former origin promotes replication in mammalian cells (e.g., COS cells) expressing the SV40 T antigen, while the latter origin promotes replication in E. coli cells.

Figure 1A:
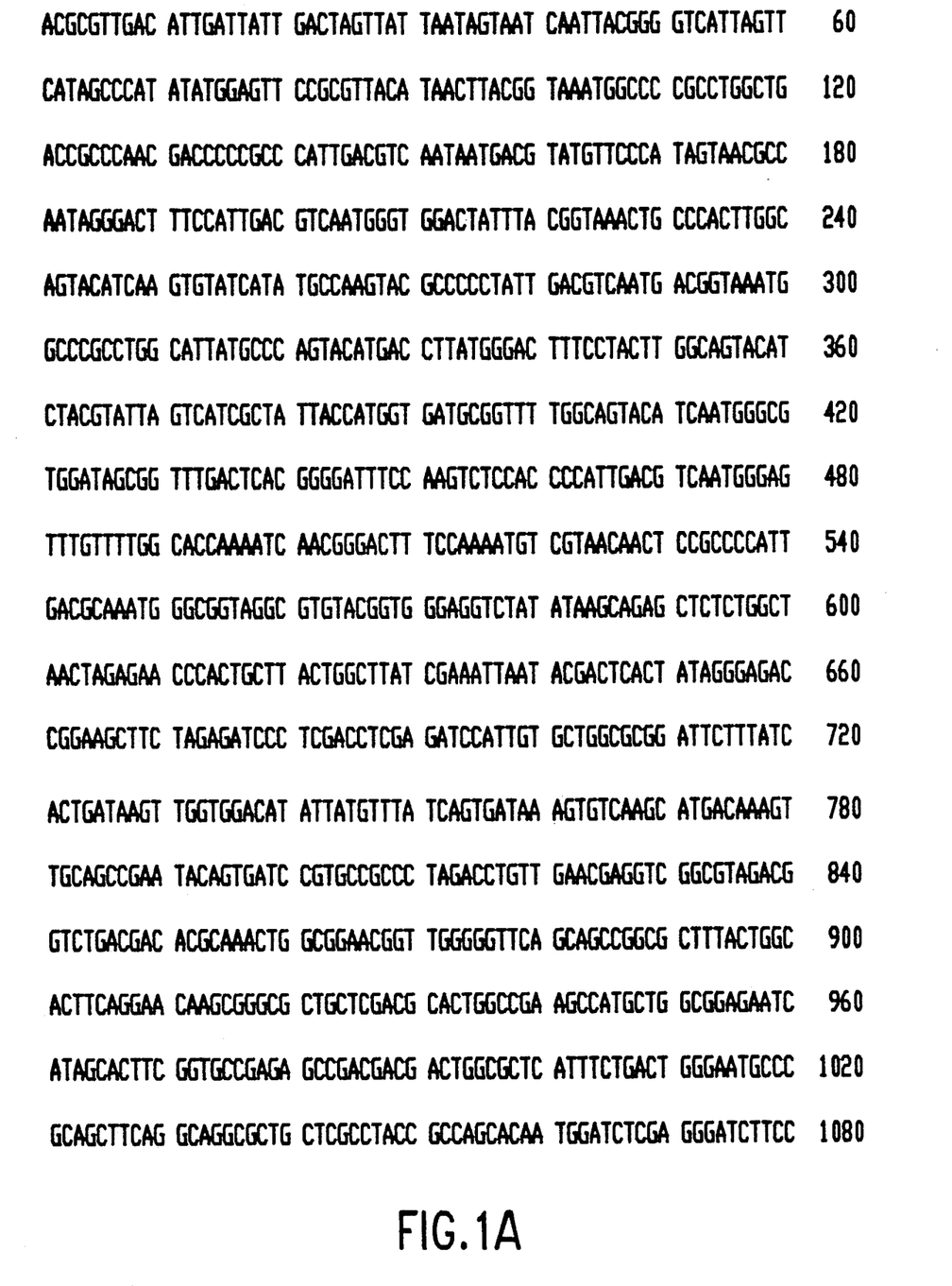
Figure 1B:
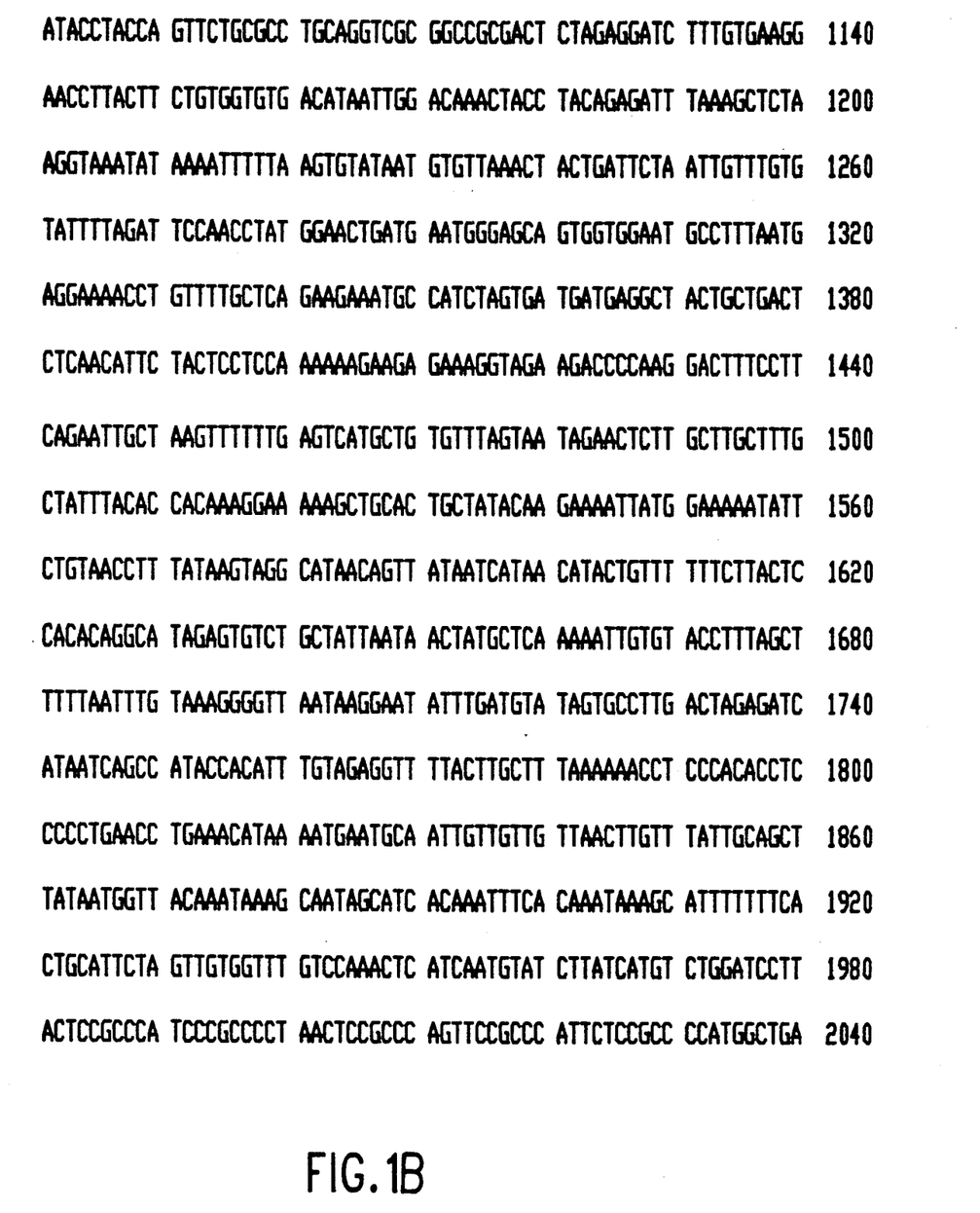
Figure 1C:
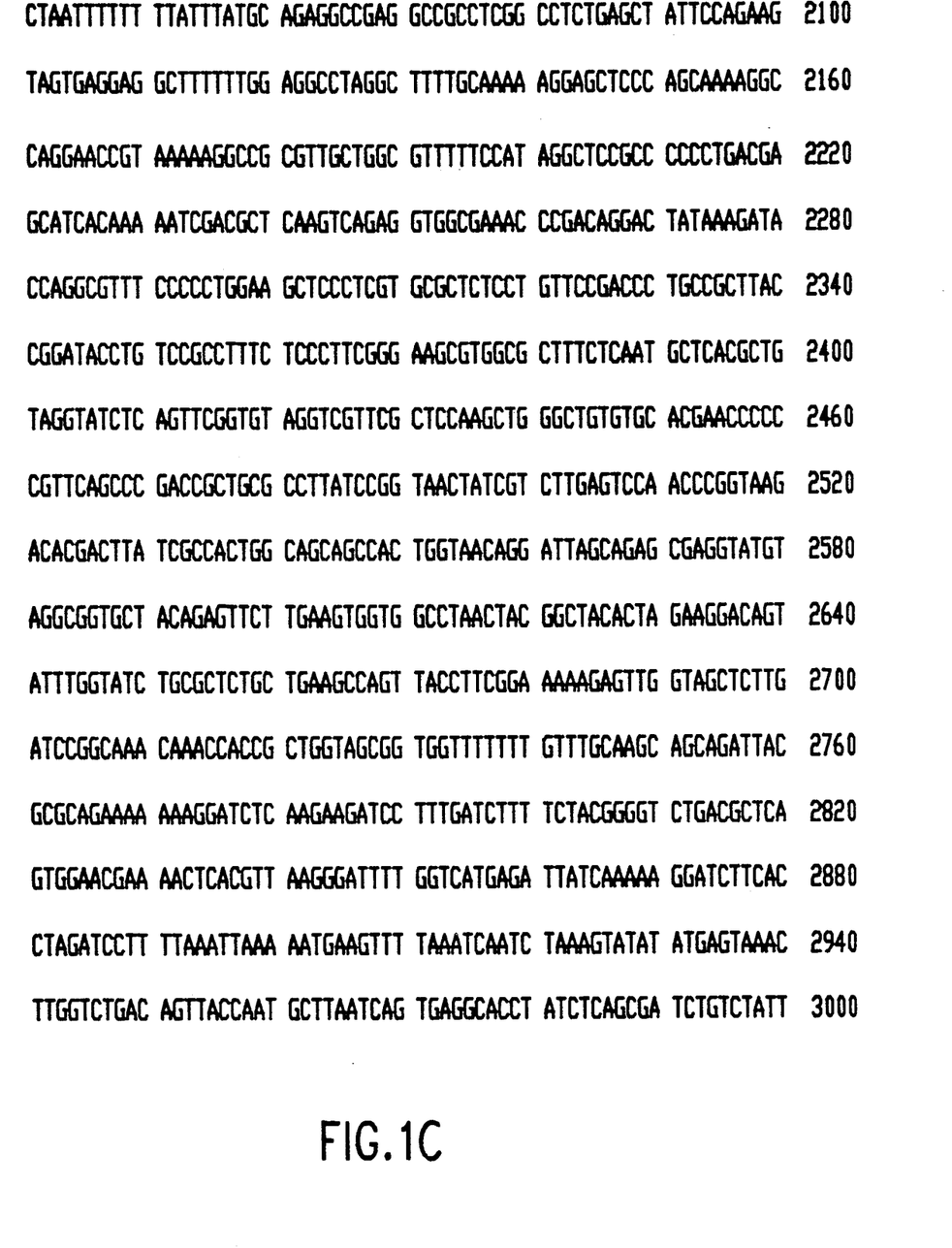
Figure 1D:
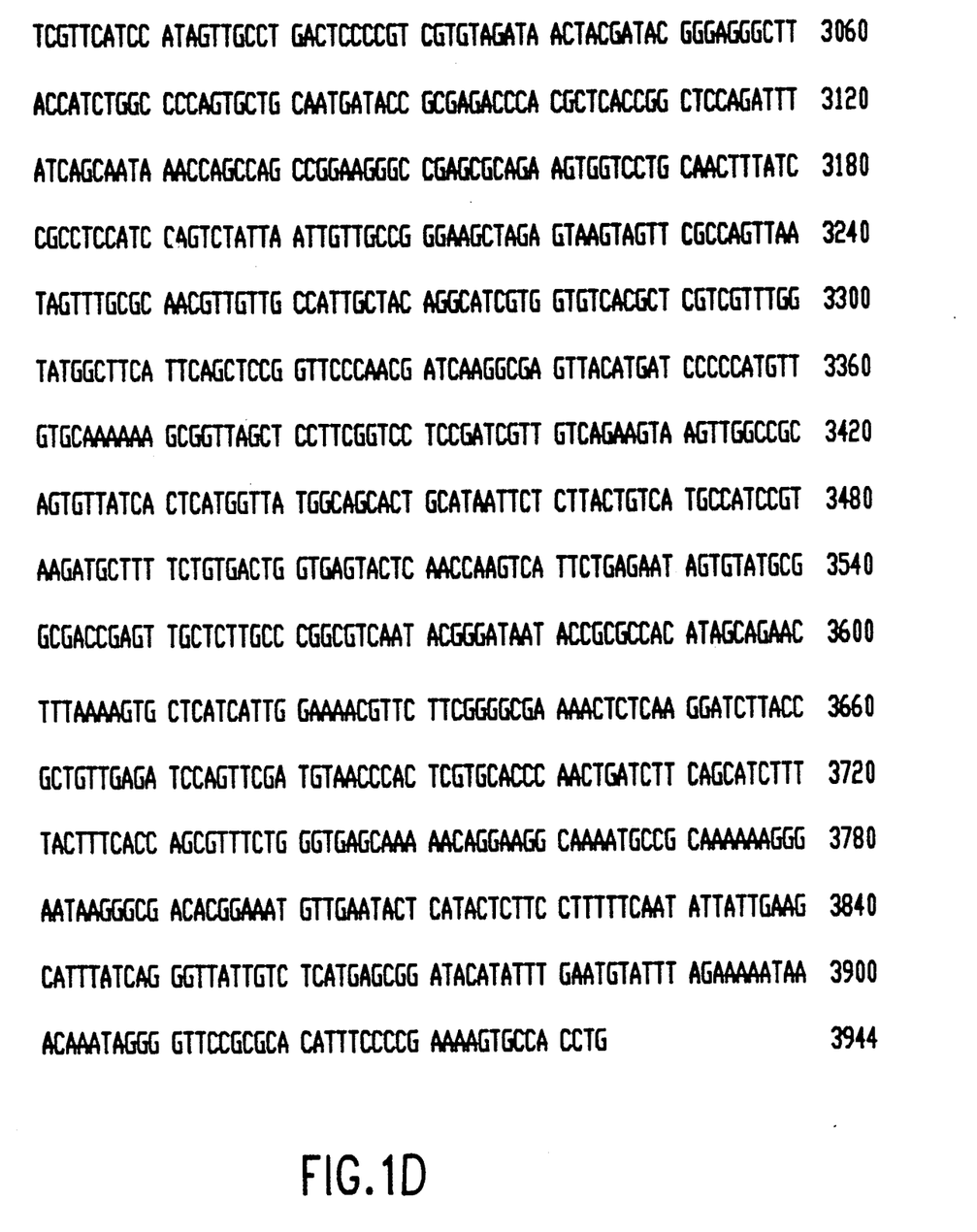
Figure 2:
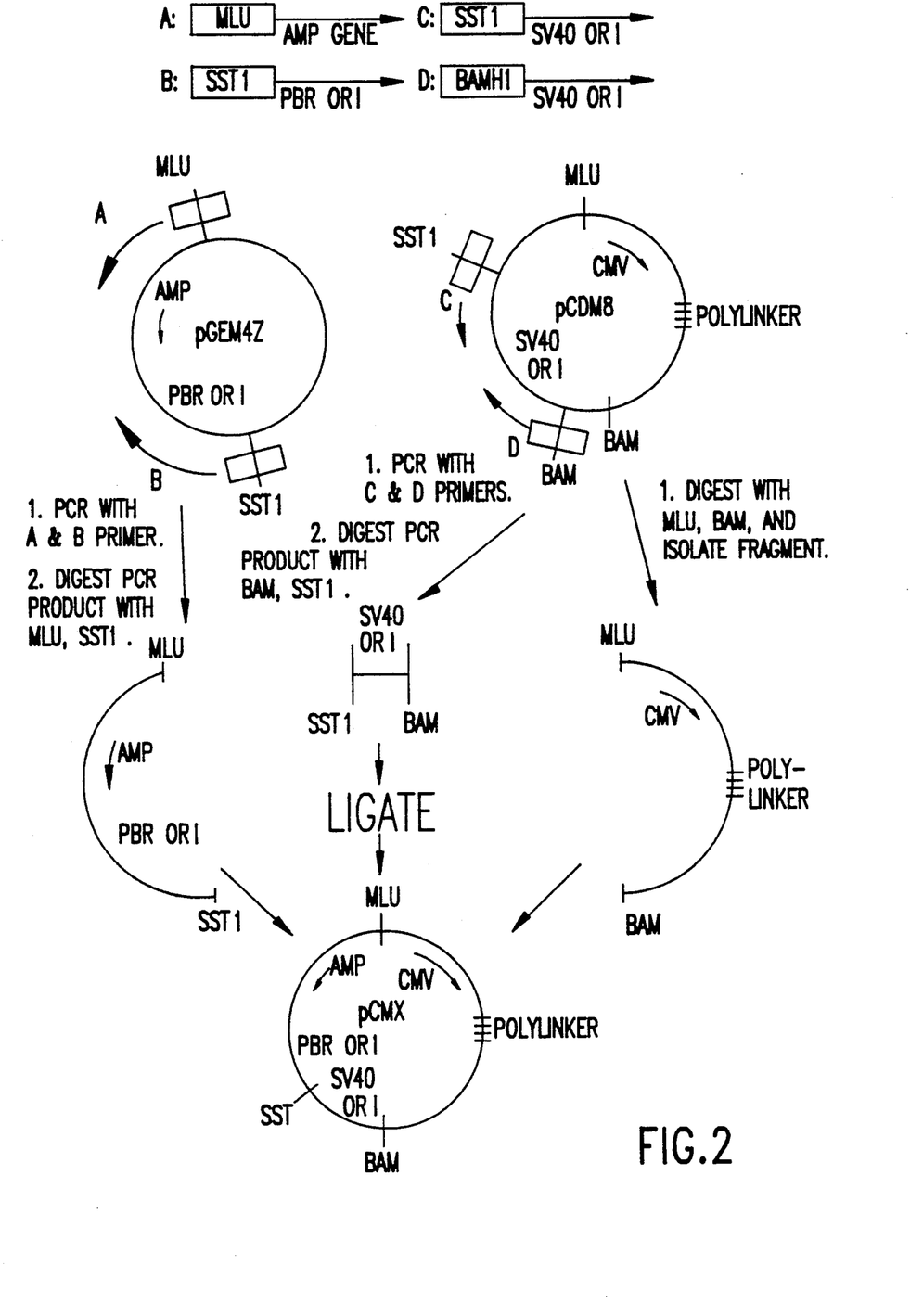
FIG. 2: Construction of pCMX from parental vectors CDM8 and pGEM4Z (see infra for details)

Four substantial differences exist between pCMX and its parent plasmid, CDM8. First, the gene encoding $\beta$-lactamase (conferring resistance to ampicillin) replaces the tRNA amber suppressor gene as the selectable marker in E. coli. The $\beta$-lactamase gene was derived from pGEM4Z (a plasmid commercially available from Promega Corp.). The portion of pGEM4Z utilized in the construction of pCMX is also found in a previous series of plasmids, such as pUC (Yanisch-Perron, et al., 1985, Gene 33:103–109) based derivatives. This origin was introduced together with the $\beta$-lactamase gene from pGEM4Z using PCR. Second, the origin of replication from the single-stranded bacteriophage, M13, has been removed. The M13 origin of replication contains cis-acting sequences promoting single-stranded DNA production from double stranded plasmid template. Single stranded DNA has been utilized for years as the template of choice for the dideoxy method of DNA sequencing. However, recent advances in recombinant DNA techniques allow for direct and efficient sequencing from a double stranded plasmid template. Third, the polyoma origin of replication has been removed. This origin of replication allows for propagation of plasmids in mammalian cell lines infected with the polyoma virus. The majority of applications involving cDNA expression cloning, as well as the transient and stable expression of genes of interest, in mammalian cell lines are adequately met utilizing COS cell types. Therefore, the polyoma origin was deemed unnecessary and was removed during the construction of pCMX. Replacement of the tRNA amber suppressor gene (200 bp) with the $\beta$-lactamase gene and pBR origin of replication (1050 bp) and removal of the M13 origin (600 bp) and polyoma origin (800 bp) result in a pCMX vector that is 550 bp smaller (12% reduction) than CDM8 (FIG. 2).

The vector, pCMX, allows for cDNA expression cloning, as well as the overexpression of genes of interest in mammalian cell lines.

6. EXAMPLES

6.1 Materials and Methods

6.1.1. Construction of pCMX

The eukaryotic expression plasmid, pCMX (FIGS. 1A–1D), was constructed as described schematically in FIG. 2. Briefly, an Sst1 and a BamHI restriction site were generated flanking the SV40 origin of replication via the polymerase chain reaction (PCR) (FIG. 2; primer C and D). The PCR product was isolated and digested with Sst1/BamHI to create a fragment flanked by these two sites. This fragment contains the SV40 origin of replication from CDM8 but lacks the polyoma origin, M13 origin and tRNA suppressor gene (supF) contained within the BamHI/MluI fragment of CDM8. Primers A and B were used with pGEM4Z to generate a PCR product that contains the $\beta$-lactamase gene and the pBR322 origin of replication. Primer A introduces an MluI site while primer B introduces an Sst1 site. This MluI/SstI fragment was introduced into a triple ligation with the Sst1/BamHI fragment containing the SV40 origin of replication and CDM8 digested with BamHI/MluI (which comprises the transcriptional unit); resulting in pCMX (FIG. 2).

6.1.2. Construction of CDM8:NGF-MYC and pCMX:NGF-MYC

Figure 3:
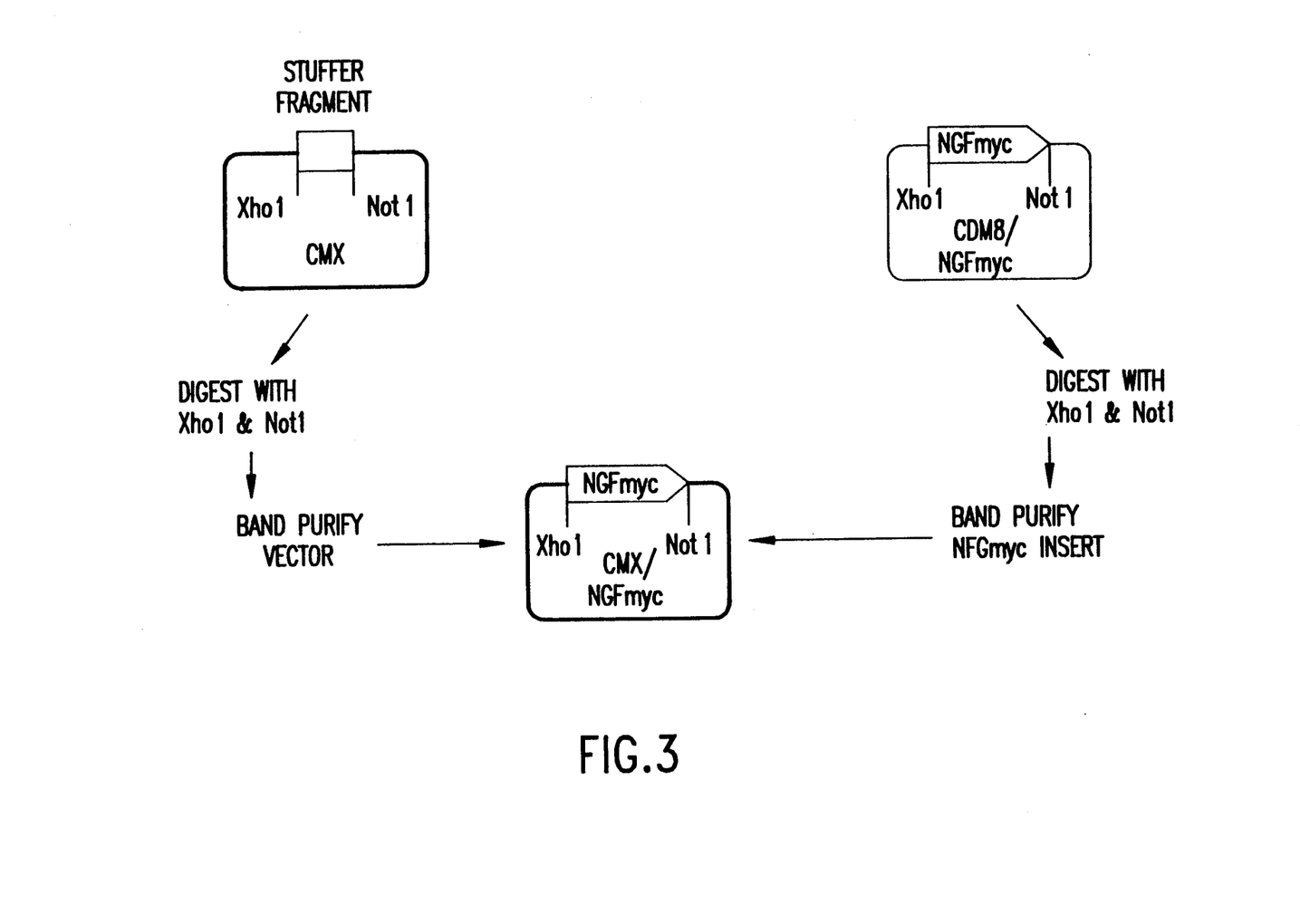
FIG. 3: Construction of CMX:NGF-myc from CDM8:NGF-myc and pCMX (see infra for details)

The patch PCR technique was used to generate a PCR product containing the mouse NGF gene (kindly provided by Drs. E. Shooter and U. Suter, Stanford University) linked, through a bridge encoding two glycines, to a sequence encoding the 10 amino acid myc epitope (Squinto, et al., 1990, Neuron 5:757-766). The primers were designed to result in a PCR product in which the last two codons of the native NGF gene were deleted due to possibility that the amino acids encoded by these codons would represent a proteolytic cleavage site that would result in the loss of the myc epitope. The PCR product was then digested with Xho1 and subcloned into the CDM8 expression plasmid to generate the expression plasmid CDM8:NGF-myc (FIG. 3) as deposited with the ATCC under the accession number 40825 and strain designation pC8-LmN-3'MYC. The NGF-myc insert was excised from CDM8 with the enzymes XhoI and NotI and subcloned into XhoI/NotI-digested pCMX, yielding the plasmid pCMX:NGF-myc (FIG. 3).

6.1.3. Transfection of COSM5 Cells with pCMX:NGF-MYC and CDM8:NGF-MYC

COSM5 cells were transfected using a DEAE-dextran protocol (Maniatis, et al, supra). Twenty four hours prior to transfection, exponentially growing COSM5 cells were harvested by trypsinization and replated at a density of $1.5 \times 10^5$ cells/35 mm dish in complete growth media. The cultures were incubated for approximately 24 hours at 37C.° in a 5% $CO_2$ incubator. For a 35 mm dish, the medium was aspirated off and 1 ml of transfection media was immediately added to the culture dish (transfection media is: RPMI (serum free)/400 µg/ml DEAE/100 µM chloroquine/1×glutamine/1x ITS[Ten nanograms to 10 micrograms of DNA to be transfected was added, the culture dish swirled several times and placed at 37° C. in a 5% $CO_2$ incubator for 3-3.5 hr. Cells routinely appeared slightly vacuolated subsequent to the incubation. The transfection medium was replaced with an equal volume of PBS/10% DMSO for 2-3 minutes. This medium was then replaced with growth medium (10% FBS in Dulbecco's modified Eagles medium [DMEM]) and incubated further at 37° C. at 5% $CO_2$ for 2-3 days.

6.1.4. $^{35}$S-Methionine Labelling of Polypeptides in Transfected COSM5 Cells Approximately $5 \times 10^5$ COSM5 cells/60 mm dish were plated in 2.5 ml of growth medium containing 10% FBS following trypsin-EDTA treatment. The cells were then transfected with 10 µg of either CDM8:NGF-myc DNA, pCMX:NGF-myc DNA or CDM8 DNA utilizing the DEAE-dextran protocol as described, supra. The transfected cells were incubated for 48-72 hours at 37° C. in a 5% $CO_2$ incubator. The supernatant was removed, cells were washed once with 1×PBS (lacking Ca/Mg), and once with 5 ml DMEM without methionine. One milliliter of DMEM (without methionine) containing 1×ITS was added to the cells and incubation was continued at 37° C. in a 5% $COp_2$ incubator for 1 hour. To the medium was added 100 µCi of $^{35}$S-methionine and incubation was continued for 4 hours under identical conditions. Debris was removed by microcentrifugation, and the supernatant was collected and transferred to a fresh, sterile eppendorf tube and either prepared for electrophoresis or stored at −70° C. for a period of up to two weeks. Samples were prepared for electrophoresis through a 15% polyacrylamide-SDS gel by standard techniques (see Maniatis, et.al; supra).

6.1.5. Bioassay of pCMX:NGF-MYC and CDM8:NGF-MYC COS Cell Extracts in Dorsal Root Ganglion Explants COSM5 cells were transfected with either pCMX:NGF-myc DNA, CDM8:NGF-myc DNA or mock-transfected (no DNA) were collected by centrifugation. Cell supernatants were prepared. Biological activity of the supernatants were assayed on explants of chick embryo dorsal root ganglia (DRG) as described in Lindsay and Rohrer (1985, Devel. Biol. 112:30). Briefly, DRG were dissected from chick embryos of 10 days incubation (E10) and 5-6 ganglia were explanted in 1 ml of a collagen gel matrix in 35 mm tissue culture dishes. After the gel had set, 1 ml of tissue culture growth medium F14 (Imperial Labs. U.K.) supplemented with 5% heat-inactivated horse serum (GIBCO) was added before addition of varying amounts of transfected COS cell supernatants. In explant cultures, the activity of respective COS cell extracts was determined by assessing the extent of fiber outgrowth in treated cultures compared to controls. Fiber outgrowth was scored on a scale of 0 to 5+, by comparing cultures photographs of a dose-response of explanted DRG and cultured with increasing amounts of NGF. In all cases results were derived from triplicate cultures.

6.1.6. Construction of a CNTF-Receptor Expression Library

SH-SY5Y cells (originally obtained from Dr. June Biedler) were used as a source of mRNA for construction of a cDNA library using the pCMX expression vector. Inserts for the cDNA library (see Section 2 for discussion) were selected on an agarose gel for sizes larger than 1 kb. The expression library was utilized to evaluate the efficiency of pCMX in expression cloning. As a working example, but not a limitation, cDNA clones expressing the ciliary neurotrophic factor receptor gene were isolated (infra. Section 6.1.8).

6.1.7. "Panning" Method

The "panning" method developed by Seed and Aruffo (1987, Proc. Natl. Acad. Sci. U.S.A. 84:3365-3369) was modified as follows: Instead of incubating the cells with antibodies recognizing the receptor, cells were incubated first with a modified form of rat CNTF engineered to contain a polypeptide epitope of the human C-myc protein (designated CNTF-myc). The ligand was used at 1 µg/ml and incubation was carried out on ice for 30 minutes; cells were then spun through PBS/2% Ficoll to remove excess ligand, and then incubated with the anti-myc monoclonal antibody 9E10 (obtained from Oncogene Sciences, Manhasset, N.Y.) for 30 minutes on ice. This was followed by another spin through PBS/2% Ficoll and "panning" on plates coated with goat antimouse IgG antibody obtained from Sigma. The plates were prepared as follows: Bacteriological 60 mm plates (Falcon 1007 or the equivalent), or 10 cm dishes such as Fisher 8-757-12 were coated with goat anti-mouse antibody, diluted to 10 µg/ml per ml in 50 mM Tris-HCl, pH 9.5. Three ml of antibody was used to coat each 6 cm dish, or 10 ml was used per 10 cm dish; plates were exposed to antibody for about 1.5 hours, then antibody was removed to the next dish, allowed to stand for 1.5 hours, and then removed again to a third dish. Plates were washed three times with 0.15 M NaCl (a wash bottle is convenient for this), and incubated with 3 ml of 1 mg/ml BSA in PBS overnight. In particular, "panning" was performed as follows: Cells were cultured in 60 mm dishes. Medium was aspirated from each dish, and 2 ml PBS/0.5 mM EDTA/0.02% azide was added and the mixture was incubated at 37° C. for 30 min. to detach cells from the dish. The cells were triturated vigorously with a short pasteur pipet, collected from each dish in a centrifuge tube, and spun 4 min. at 200×g. Cells were resuspended in 0.5-1.0 ml PBS/EDTA/azide/5% FBS and incubated with CNTF:myc for 30 min. on ice. An equal volume of PBS/EDTA/azide was layered carefully on 3 ml PBS/EDTA/azide/2% Ficoll, spun 4 min. at 200×g, and the supernatant was aspirated in one smooth movement. The cells were then incubated with 9E10 antibody for 30 minutes on ice, and the spin through PBS/EDTA/azide/2% Ficoll was repeated. The cells were taken up in 0.5 ml PBS/EDTA/azide/5% FBS by pipetting through 100 micron Nylon mesh (Tetko). Cells were added from at most two 60 mm dishes to one 60 mm goat anti-mouse Ig antibody coated plate, and allowed to sit at room temperature 1-3 hours. Excess cells not adhering to dish were removed by gentle washing with PBS/5% serum or with medium (2 or 3 washes of 3 ml were usually sufficient).

6.1.8. Identification of Clones Containing the Ciliary Neurotrophic Factor Receptor Gene Plasmid DNA from the expression library was transfected into COSM5 cells (approximately 250–500 ng per 100 mm dish; 2 dishes were transfected), using DEAE/-chloroquine according to standard procedures. Two days after transfection, cells were detached from their dishes and subjected to the Aruffo/Seed panning procedure modified as described supra.

After washing nonadhering cells from the plates, Hirt supernatants were prepared, and plasmid DNA was precipitated in the presence of 10–20 μg of tRNA. The resulting DNA was introduced into DH10B bacteria by electroporation (Electromax, BRL) according to the manufacturer's instructions. Cultures grown from the electroporated bacteria were used to prepare plasmid DNA for another round of transfection and panning; a plate of COS cells transfected with this plasmid DNA clearly revealed a large number of COS cells expressing the CNTFR by an indirect iodinated-antibody binding assay (carried out according to Section 6.1.9). After a second round of panning/plasmid DNA isolation/electroporation on these transfectants, the bacterial transformants resulting from the electroporation step were plated out on ampicillin plates. Fifteen individual bacterial colonies were picked, and plasmid DNA prepared from each of the clones were transfected individually into COS cells for assay.

6.1.9. Indirect $^{125}$I Goat Anti-mouse Antibody Binding Assay

COS cells were transfected with plasmid DNA from the library, the enriched library, or individual clones. After 48 hours, cells were incubated sequentially for 30 minutes on ice with PBS (with Ca, Mg)/5% FBS containing:

1) 1 μg/ml CNTF-myc;
2) 10 μg/ml 9E10;
3) $^{125}$I goat anti-mouse antibody (GaM) (0.5–1 μCi/ml).

Cells were washed 3×5 minutes in PBS/5% FBS after each step. After the last wash, the plates were autoradiographed.

For the individual clones, a quantitative estimate of total radioactivity bound was made with a hand-held gamma counter.

6.1.10. Fluorescence Activated Cell-sorting Analysis

Transfected COS cells were incubated sequentially with CNTF-myc, 9E10 antibody, and FITC-labelled goat anti-mouse antibody. Then they were detached from dishes and subjected to FACS analysis. COS cells transfected with a CNTF-receptor expressing plasmid contain a large subpopulation displaying greatly increased fluorescence by this assay.

6.2. Results

Figure 4:
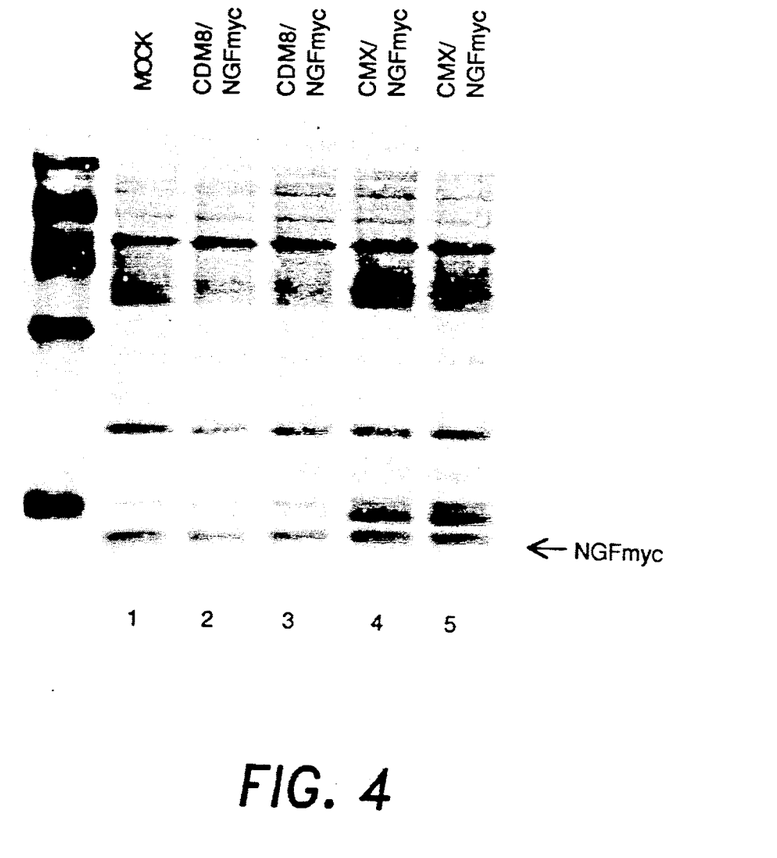
FIG. 4: Autoradiograph of $^{35}$S-Methionine labeled proteins from COS cells transfected with:
Lane 1: No DNA (Mock Transfection),
Lane 2: CDM8:NGF-myc,
Lane 3: CDM8:NGF-myc,
Lane 4: pCMX:NGF-myc,
Lane 5: pCMX:NGF-myc,
(See infra for details).

6.2.1 Comparative Expression of pCMX:NGF-MYC and CDM8:NGF-MYC $^{35}$S-Methionine labelled COSM5 cells were collected as described, supra. Equal amounts of COSM5 cell supernatants from mock transfected cells (FIG. 4, lane 1), cells transfected with CDM8:NGF-myc DNA (FIG. 4, lanes 2+3) or pCMX:NGF-myc DNA (lanes 4+5) were electrophoresed through a 15% polyacrylamide-SDS gel and subjected to autoradiography. The auto-radiograph was analyzed by scanning densitometry. The level of expression of NGF-myc in COSM5 cells transfected with pCMX:NGF-myc was approximately 8–10 fold higher than in COSM5 cells transfected with CDM8:NGF-myc (compare Lanes 4+5 with lanes 2+3 [see arrow]). Also, note the complete lack of NGF-myc expression in COSM5 cells transfected with pCMX minus the NGF-myc insert.

Bioactivity of COSM5 cell supernatants on DRG explants is presented in Table I.

TABLE I

| Bioactivity of COS cell supernatants on DRG explants | |
|---|---|
| | Neurite outgrowth |
| Positive Control* | 5+,5,4,4,4 |
| Mock Transfected | |
| 50 μl | 0,0,0,1,1 |
| CDM8:NGF-myc: | |
| 50 μl | 5+,5+,5+,5+,1 |
| 20 μl | 5,5,5,5,5 |
| 10 μl | 2,3,3,4,4 |
| 5 μl | 2,3,2,2,3 |
| 1 μl | 1,1,1,2,2 |
| CMX:NGF-myc: | |
| 50 μl | 5+,5+,5+,5+,5+ |
| 20 μl | 5+,5+,5+,5+,5+ |
| 10 μl | 5,5,5,5,5+ |
| 5 μl | 3,4,4,4,4 |
| 1 μl | 1,1,1,2,2 |

*NGF at 5 ng/ml

Increasing amounts of extract from pCMX:NGF-myc and CDM8:NGF-myc were tested. The most notable effect was observed when either 5 μl or 10 μl of either supernatant is tested. In such a case, approximately a two to four-fold increase in NGF-myc activity was observed in supernatants from CMX:NGF-myc transfected COSM5 cells, as compared with the pCDM8:NGF-myc transfected COSM5 cell supernatants.

Therefore, expression of stable protein as well as the biological activity of said protein was substantially greater in pCMX:NGF-myc transfected cells than with CDM8:NGF-myc transfected cells.

6.2.2 Isolation of cDNA Encoding CNTFR

Out of 15 plasmids tested as described supra, 14 resulted in transfected COS cells expressing CNTF binding sites as determined by a variety of assays, including the indirect antibody binding assay and fluorescence activated cell sorting (FACS) analysis described infra.

Restriction analysis of the 14 positive clones showed that they fell into four classes. Members of each class produced an identical pattern of bands on digestion with the enzyme Pst1. Further restriction analysis revealed that the four classes of clones overlapped, and preliminary sequence data confirmed that they shared overlapping sequences at their 5' ends.

To characterize the proteins coded for by the four classes of clones, they were all transcribed from the T7 promoter in the 5' region of the vector polylinker. After in vitro translation, the products were electrophoresed on a polyacrylamide gel. Class (a) produced no protein, since it is in the wrong orientation with respect to the T7 promoter. The other three classes all produced proteins of identical sizes (approximately 42 kd), verifying that they encoded the same protein. This demonstrates that pCMX performed reliably in the isolation of 4 independent clones of the CNTFR. Additional results confirmed the existence of cDNAs encoding the CNTFR, as shown by indirect antibody binding assay and fluoresence activated cell sorting "(FACS)" analysis (see copending application entitled "Ciliary Neurotrophic Factor Receptor" filed on even date herewith, and incorporated by reference herein).

7. DEPOSIT OF MICROORGANISMS

The following microorganisms were deposited with the Agricultural Research Culture Collection (NRRL), Northern Regional Research Center, 1815 North University St., Peoria, Ill., 61604, on Mar. 26, 1991 and given accession numbers as follows:

| Strain | Plasmid | Accession No. |
|---|---|---|
| E. coli DH5αF1 carrying | pCMX | NRRL B-18790 |

The plasmid DNA expression vector CDM8:NGF-myc was previously deposited with the ATCC with the accession numbers 40825 (strain designation pC8-LmN-3'MYC) and 40864 (strain designation pC8/mN/MYC-NM1).

The present invention is not to be limited in scope by the microorganisms deposited or the embodiments disclosed in the examples which are intended as illustrations of a few aspects of the invention, and any embodiments which are functionally equivalent are within the scope of this invention. Indeed, various modifications of the invention in addition to those shown and described herein will become apparent to those skilled in the art and are intended to fall within the scope of the appended claims.

Various references are cited herein, the disclosures of which are incorporated by reference in their entireties.

What is claimed is:

1. The DNA vector pCMX as deposited with the NRRL, having accession number NRRL B-18790.

2. The DNA vector of claim 1 further comprising a structural gene inserted in the 5'→3' orientation within the polylinker sequence.

3. The DNA vector of claim 1 further comprising a structural gene inserted in the 3'→5' orientation within the polylinker sequence.

4. The DNA vector of claim 1 further comprising a structural gene which encodes NGF-myc inserted in the 5'→3' orientation within the polylinker sequence.

5. The DNA vector of claim 1 in which the T7 phage RNA polymerase promoter is fused downstream from the early immediate HCMV promoter region.

6. The DNA vector pCMX:NGF-myc.

7. A DNA vector comprising pCMX:NGF-myc.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 3944 base pairs
( B ) TYPE: nucleic acid
( C ) STRANDEDNESS: double
( D ) TOPOLOGY: circular ( i i ) MOLECULE TYPE: cDNA ( x i ) SEQUENCE DESCRIPTION: SEQ ID NO:1:

| | | | | | | |
|---|---|---|---|---|---|---|
| ACGCGTTGAC | ATTGATTATT | GACTAGTTAT | TAATAGTAAT | CAATTACGGG | GTCATTAGTT | 60 |
| CATAGCCCAT | ATATGGAGTT | CCGCGTTACA | TAACTTACGG | TAAATGGCCC | CGCCTGGCTG | 120 |
| ACCGCCCAAC | GACCCCCGCC | CATTGACGTC | AATAATGACG | TATGTTCCCA | TAGTAACGCC | 180 |
| AATAGGGACT | TTCCATTGAC | GTCAATGGGT | GGACTATTTA | CGGTAAACTG | CCCACTTGGC | 240 |
| AGTACATCAA | GTGTATCATA | TGCCAAGTAC | GCCCCCTATT | GACGTCAATG | ACGGTAAATG | 300 |
| GCCCGCCTGG | CATTATGCCC | AGTACATGAC | CTTATGGGAC | TTTCCTACTT | GGCAGTACAT | 360 |
| CTACGTATTA | GTCATCGCTA | TTACCATGGT | GATGCGGTTT | TGGCAGTACA | TCAATGGGCG | 420 |
| TGGATAGCGG | TTTGACTCAC | GGGGATTTCC | AAGTCTCCAC | CCCATTGACG | TCAATGGGAG | 480 |
| TTTGTTTTGG | CACCAAAATC | AACGGGACTT | TCCAAAATGT | CGTAACAACT | CCGCCCCATT | 540 |
| GACGCAAATG | GGCGGTAGGC | GTGTACGGTG | GGAGGTCTAT | ATAAGCAGAG | CTCTCTGGCT | 600 |
| AACTAGAGAA | CCCACTGCTT | ACTGGCTTAT | CGAAATTAAT | ACGACTCACT | ATAGGGAGAC | 660 |
| CGGAAGCTTC | TAGAGATCCC | TCGACCTCGA | GATCCATTGT | GCTGGCGCGG | ATTCTTTATC | 720 |
| ACTGATAAGT | TGGTGGACAT | ATTATGTTTA | TCAGTGATAA | AGTGTCAAGC | ATGACAAAGT | 780 |
| TGCAGCCGAA | TACAGTGATC | CGTGCCGCCC | TAGACCTGTT | GAACGAGGTC | GGCGTAGACG | 840 |
| GTCTGACGAC | ACGCAAACTG | GCGGAACGGT | TGGGGGTTCA | GCAGCGGCG | CTTTACTGGC | 900 |
| ACTTCAGGAA | CAAGCGGGCG | CTGCTCGACG | CACTGGCCGA | AGCCATGCTG | GCGGAGAATC | 960 |
| ATAGCACTTC | GGTGCCGAGA | GCCGACGACG | ACTGGCGCTC | ATTTCTGACT | GGGAATGCCC | 1020 |
| GCAGCTTCAG | GCAGGCGCTG | CTCGCCTACC | GCCAGCACAA | TGGATCTCGA | GGGATCTTCC | 1080 |
| ATACCTACCA | GTTCTGCGCC | TGCAGGTCGC | GGCCGCGACT | CTAGAGGATC | TTTGTGAAGG | 1140 |
| AACCTTACTT | CTGTGGTGTG | ACATAATTGG | ACAAACTACC | TACAGAGATT | TAAAGCTCTA | 1200 |

| | | | | | |
|---|---|---|---|---|---|
| AGGTAAATAT | AAAATTTTTA | AGTGTATAAT | GTGTTAAACT | ACTGATTCTA | ATTGTTTGTG | 1260 |
| TATTTTAGAT | TCCAACCTAT | GGAACTGATG | AATGGGAGCA | GTGGTGGAAT | GCCTTTAATG | 1320 |
| AGGAAAACCT | GTTTTGCTCA | GAAGAAATGC | CATCTAGTGA | TGATGAGGCT | ACTGCTGACT | 1380 |
| CTCAACATTC | TACTCCTCCA | AAAAGAAGA | GAAAGGTAGA | AGACCCCAAG | GACTTTCCTT | 1440 |
| CAGAATTGCT | AAGTTTTTG | AGTCATGCTG | TGTTAGTAA | TAGAACTCTT | GCTTGCTTTG | 1500 |
| CTATTTACAC | CACAAAGGAA | AAAGCTGCAC | TGCTATACAA | GAAAATTATG | GAAAAATATT | 1560 |
| CTGTAACCTT | TATAAGTAGG | CATAACAGTT | ATAATCATAA | CATACTGTTT | TTTCTTACTC | 1620 |
| CACACAGGCA | TAGAGTGTCT | GCTATTAATA | ACTATGCTCA | AAAATTGTGT | ACCTTTAGCT | 1680 |
| TTTTAATTTG | TAAAGGGGTT | AATAAGGAAT | ATTTGATGTA | TAGTGCCTTG | ACTAGAGATC | 1740 |
| ATAATCAGCC | ATACCACATT | TGTAGAGGTT | TTACTTGCTT | TAAAAAACCT | CCCACACCTC | 1800 |
| CCCCTGAACC | TGAAACATAA | AATGAATGCA | ATTGTTGTTG | TTAACTTGTT | TATTGCAGCT | 1860 |
| TATAATGGTT | ACAAATAAAG | CAATAGCATC | ACAAATTTCA | CAAATAAAGC | ATTTTTTCA | 1920 |
| CTGCATTCTA | GTTGTGGTTT | GTCCAAACTC | ATCAATGTAT | CTTATCATGT | CTGGATCCTT | 1980 |
| ACTCCGCCCA | TCCCGCCCCT | AACTCCGCCC | AGTTCCGCCC | ATTCTCCGCC | CCATGGCTGA | 2040 |
| CTAATTTTTT | TTATTTATGC | AGAGGCCGAG | GCCGCCTCGG | CCTCTGAGCT | ATTCCAGAAG | 2100 |
| TAGTGAGGAG | GCTTTTTTGG | AGGCCTAGGC | TTTTGCAAAA | AGGAGCTCCC | AGCAAAGGC | 2160 |
| CAGGAACCGT | AAAAAGGCCG | CGTTGCTGGC | GTTTTTCCAT | AGGCTCCGCC | CCCCTGACGA | 2220 |
| GCATCACAAA | AATCGACGCT | CAAGTCAGAG | GTGGCGAAAC | CCGACAGGAC | TATAAAGATA | 2280 |
| CCAGGCGTTT | CCCCCTGGAA | GCTCCCTCGT | GCGCTCTCCT | GTTCCGACCC | TGCCGCTTAC | 2340 |
| CGGATACCTG | TCCGCCTTTC | TCCCTTCGGG | AAGCGTGGCG | CTTTCTCAAT | GCTCACGCTG | 2400 |
| TAGGTATCTC | AGTTCGGTGT | AGGTCGTTCG | CTCCAAGCTG | GGCTGTGTGC | ACGAACCCCC | 2460 |
| CGTTCAGCCC | GACCGCTGCG | CCTTATCCGG | TAACTATCGT | CTTGAGTCCA | ACCCGGTAAG | 2520 |
| ACACGACTTA | TCGCCACTGG | CAGCAGCCAC | TGGTAACAGG | ATTAGCAGAG | CGAGGTATGT | 2580 |
| AGGCGGTGCT | ACAGAGTTCT | TGAAGTGGTG | GCCTAACTAC | GGCTACACTA | GAAGGACAGT | 2640 |
| ATTTGGTATC | TGCGCTCTGC | TGAAGCCAGT | TACCTTCGGA | AAAAGAGTTG | GTAGCTCTTG | 2700 |
| ATCCGGCAAA | CAAACCACCG | CTGGTAGCGG | TGGTTTTTTT | GTTTGCAAGC | AGCAGATTAC | 2760 |
| GCGCAGAAAA | AAAGGATCTC | AAGAAGATCC | TTTGATCTTT | TCTACGGGGT | CTGACGCTCA | 2820 |
| GTGGAACGAA | AACTCACGTT | AAGGGATTTT | GGTCATGAGA | TTATCAAAAA | GGATCTTCAC | 2880 |
| CTAGATCCTT | TTAAATTAAA | AATGAAGTTT | TAAATCAATC | TAAAGTATAT | ATGAGTAAAC | 2940 |
| TTGGTCTGAC | AGTTACCAAT | GCTTAATCAG | TGAGGCACCT | ATCTCAGCGA | TCTGTCTATT | 3000 |
| TCGTTCATCC | ATAGTTGCCT | GACTCCCCGT | CGTGTAGATA | ACTACGATAC | GGGAGGGCTT | 3060 |
| ACCATCTGGC | CCCAGTGCTG | CAATGATACC | GCGAGACCCA | CGCTCACCGG | CTCCAGATTT | 3120 |
| ATCAGCAATA | AACCAGCCAG | CCGGAAGGGC | CGAGCGCAGA | AGTGGTCCTG | CAACTTTATC | 3180 |
| CGCCTCCATC | CAGTCTATTA | ATTGTTGCCG | GGAAGCTAGA | GTAAGTAGTT | CGCCAGTTAA | 3240 |
| TAGTTTGCGC | AACGTTGTTG | CCATTGCTAC | AGGCATCGTG | GTGTCACGCT | CGTCGTTTGG | 3300 |
| TATGGCTTCA | TTCAGCTCCG | GTTCCCAACG | ATCAAGGCGA | GTTACATGAT | CCCCCATGTT | 3360 |
| GTGCAAAAAA | GCGGTTAGCT | CCTTCGGTCC | TCCGATCGTT | GTCAGAAGTA | AGTTGGCCGC | 3420 |
| AGTGTTATCA | CTCATGGTTA | TGGCAGCACT | GCATAATTCT | CTTACTGTCA | TGCCATCCGT | 3480 |
| AAGATGCTTT | TCTGTGACTG | GTGAGTACTC | AACCAAGTCA | TTCTGAGAAT | AGTGTATGCG | 3540 |
| GCGACCGAGT | TGCTCTTGCC | CGGCGTCAAT | ACGGGATAAT | ACCGCGCCAC | ATAGCAGAAC | 3600 |
| TTTAAAAGTG | CTCATCATTG | GAAAACGTTC | TTCGGGGCGA | AAACTCTCAA | GGATCTTACC | 3660 |

-continued

| | | | | | |
|---|---|---|---|---|---|
| GCTGTTGAGA | TCCAGTTCGA | TGTAACCCAC | TCGTGCACCC | AACTGATCTT | CAGCATCTTT | 3720
| TACTTTCACC | AGCGTTTCTG | GGTGAGCAAA | AACAGGAAGG | CAAAATGCCG | CAAAAAAGGG | 3780
| AATAAGGGCG | ACACGGAAAT | GTTGAATACT | CATACTCTTC | CTTTTTCAAT | ATTATTGAAG | 3840
| CATTTATCAG | GGTTATTGTC | TCATGAGCGG | ATACATATTT | GAATGTATTT | AGAAAAATAA | 3900
| ACAAATAGGG | GTTCCGCGCA | CATTTCCCCG | AAAAGTGCCA | CCTG | | 3944